United States Patent
Ikeda et al.

(10) Patent No.: US 7,084,975 B2
(45) Date of Patent: Aug. 1, 2006

(54) PARTICLE DIAMETER DISTRIBUTION MEASUREMENT APPARATUS AND METHOD OF CALIBRATION

(75) Inventors: Hideyuki Ikeda, Kyoto (JP); Yuki Nakano, Kyoto (JP)

(73) Assignee: Horiba, Ltd., Kyoto (JP)

( * ) Notice: Subject to any disclaimer, the term of this patent is extended or adjusted under 35 U.S.C. 154(b) by 323 days.

(21) Appl. No.: 10/289,906

(22) Filed: Nov. 7, 2002

(65) Prior Publication Data

US 2003/0090656 A1    May 15, 2003

(30) Foreign Application Priority Data

Nov. 9, 2001 (JP) .............................. 2001-344430

(51) Int. Cl.
*G01N 15/02* (2006.01)

(52) U.S. Cl. ..................................... 356/336

(58) Field of Classification Search ........ 356/335–343; 250/573, 574, 222.2
See application file for complete search history.

(56) References Cited

U.S. PATENT DOCUMENTS 4,801,205 A    1/1989    Tatsuno
6,741,350 B1 *  5/2004   Ikeda et al. .................. 356/336

FOREIGN PATENT DOCUMENTS

JP        61-014543        1/1986

* cited by examiner

*Primary Examiner*—Tu T. Nguyen (57) ABSTRACT

A particle diameter distribution measurement apparatus and method includes a sample cell that can be irradiated by a source of light. A plurality of detectors are positioned operatively adjacent to the sample cell to measure light interacting with a specimen in the sample cell. A storage unit stores values representative of outputs of the detectors for a plurality of standard particle sizes. The representation outputs extend across a range of detection for a plurality of detectors. A controller unit can perform a calibration based on the stored values and an actual measurement of one or more standard particle sizes that has the capability of providing a range of detection that will be inclusive of a standard particle size that is not available for measurement.

9 Claims, 6 Drawing Sheets

| BASE DATA | SAMPLE1 | SAMPLE2 | SAMPLE3 | SAMPLE4 | SAMPLE5 |
|---|---|---|---|---|---|
| Ch.01(D01) | 9.90E-01 | 4.45E-01 | 4.31E-01 | 9.06E-02 | 8.56E-03 |
| Ch.02(D02) | 9.61E-01 | 5.27E-01 | 4.57E-01 | 9.99E-02 | 9.81E-03 |
| Ch.03(D03) | 9.14E-01 | 6.13E-01 | 4.82E-01 | 1.10E-01 | 1.12E-02 |
| Ch.04(D04) | 8.73650e-07 | 3.03370e-06 | 1.05690e-04 | 2.40900e-03 | 2.38000e-01 |
| Ch.05(D05) | 7.79E-01 | 7.79E-01 | 5.35E-01 | 1.32E-01 | 1.46E-02 |
| Ch.06 | 8.73650e-07 | 1.30370e-06 | 1.05690e-04 | 2.40900e-03 | 2.38000e-01 |
| Ch.07(D04) | 6.13E-01 | 9.14E-01 | 5.89E-01 | 1.57E-01 | 1.89E-02 |
| Ch.08(D05) | 5.27E-01 | 9.61E-01 | 6.16E-01 | 1.71E-01 | 2.14E-02 |
| Ch.09(D06) | 4.45E-01 | 9.90E-01 | 6.43E-01 | 1.86E-01 | 2.42E-02 |
| Ch.10(D07) | 3.68E-01 | 1.00E+00 | 6.70E-01 | 2.02E-01 | 2.73E-02 |
| Ch.11(D08) | 2.98E-01 | 9.90E-01 | 6.97E-01 | 2.18E-01 | 3.08E-02 |
| | ... | ... | ... | ... | ... |
| Ch.90(S1) | 6.64E-36 | 1.60E-28 | 2.73E-02 | 2.02E-01 | 6.70E-01 |

PARTICLE DIAMETER DISTRIBUTION MEASUREMENT APPARATUS AND METHOD OF CALIBRATION

BACKGROUND OF THE INVENTION

1. Field of the Invention

The present invention relates to a particle diameter distribution measurement apparatus of a laser diffraction/scattering type and more particularly to a calibration apparatus and method of verifying a measurement when standardized particles are not available over a full range of measurements.

2. Description of the Prior Art

Conventionally, when a particle diameter distribution is calculated by a particle diameter distribution measurement apparatus, an intensity distribution of a diffracted light or a scattered light generated by irradiating a light onto samples to be measured is calculated on the basis of detected value data from a plurality of detectors (the detectors have channels, respectively) arranged to cover the samples to be measured. However, the detectors are individually different from each other, and are also different in light-receiving area. For this reason, the sensitivities of the detectors must be individually calibrated. When the particle diameter distribution measurement apparatus has a plurality of light sources, the intensities of lights generated by respective light sources must also be calibrated.

As a calibrating method for the particle diameter distribution measurement apparatus, the following method has been used. For example, a standard particle which uses a poly styrene latex sphere (to be referred to as a PSL sphere hereinafter) and which generates a scattered light and a diffracted light which have approximately theoretical values is measured as a sample to be measured. A ratio of a detected value of the diffracted light or the scattered light obtained at this time to a reference value of the scattered light of the standard particle is stored as a calibration constant, the intensity of the scattered light from the sample is corrected on the basis of the calibration constant in the measurement of the sample. This method makes it possible to perform accurate measurement.

In general, a detector arranged in the forward direction of irradiation of a laser beam irradiated on a sample to be measured detects a diffracted/scattered light obtained by a large particle having a size of about 1 mm, and a detector arranged in the backward direction detects a diffracted light or a scattered light obtained by a small particle having a several tens nm to several μm. For this reason, in a particle diameter distribution measurement apparatus in which a measurement range of particle diameter distributions is a wide range, for example, the range of several tens nm to several mm, detectors are arranged from the front to the rear. For this reason, in order to calibrate the measurement sensitivities of all the detectors, standard particles of different types must be available and measured.

The calibration in the apparatus is also performed after maintenance such as an exchange of supplies and refinement for the particle diameter distribution measurement apparatus or after the positions of optical components. It is preferable that the calibration is periodically performed.

Figure 6:
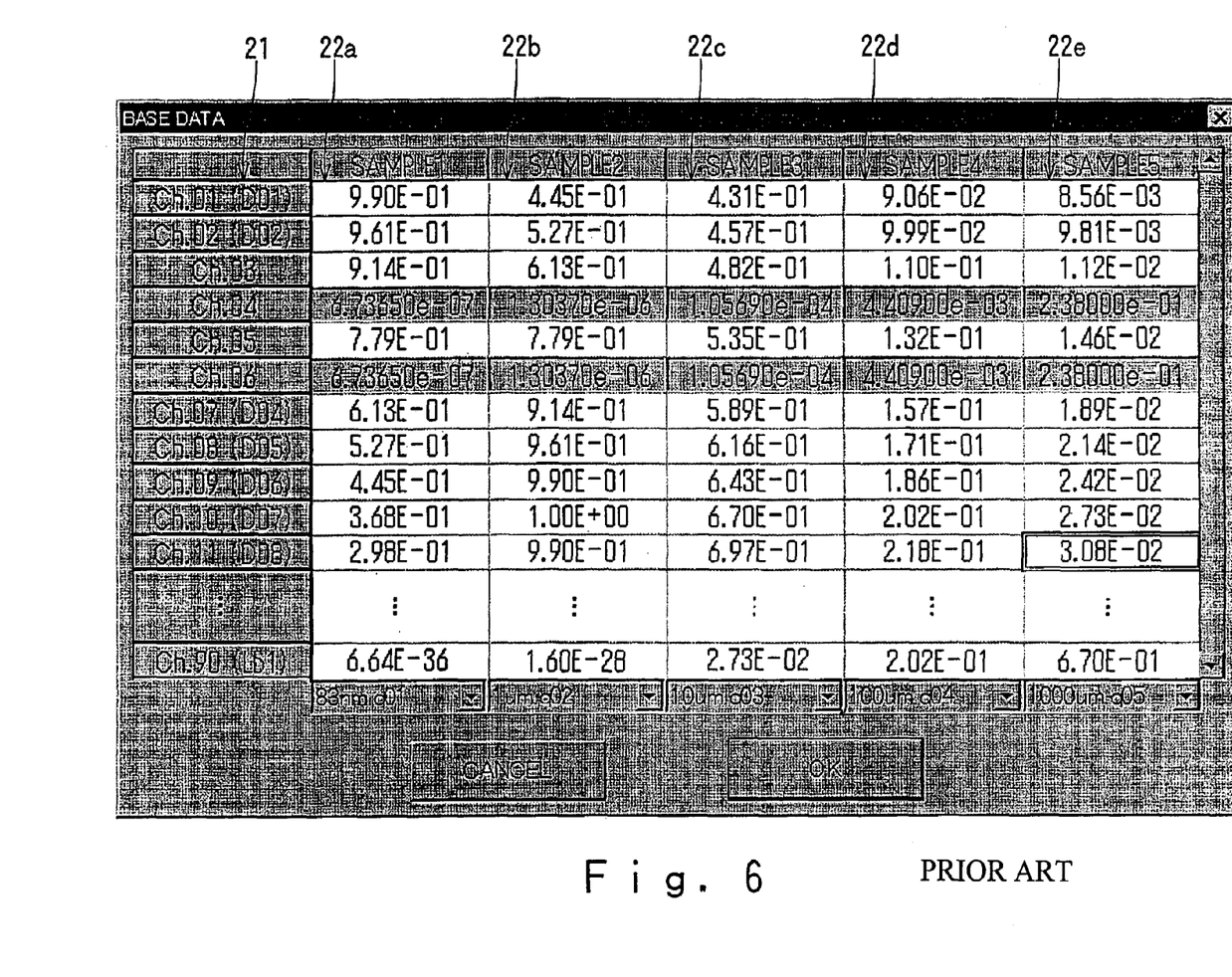
FIG. 6 is a diagram showing a screen which displays a list of standard particles in a conventional particle diameter distribution measurement apparatus.

FIG. 6 shows an example of a display screen of standard particles in a conventional particle diameter distribution measurement apparatus. In FIG. 6, PSL spheres used as standard particles in the illustrated apparatus calibration have five diameters of, for example, 1 mm, 100 μm, 10 μm, 1 μm, and 80 nm, respectively, and are expressed as "Sample 1" to "Sample 5", respectively. Reference numeral 21 denotes a channel, and reference numerals 22a to 22e denote reference values of scattered lights and diffracted lights detected by the channels of the detectors when the standard particles are used as samples to be measured.

The apparatus calibration in the particle diameter distribution measurement apparatus is performed as follows. That is, the standard particles are sequentially used and actually measured as samples to be measured. The detected values from the channels of the detectors are compared with the reference numerals 22a to 22e to calculate correction values of the detected values from the channels of the detectors, and the corrected values are stored. When samples to be measured the particle diameter distribution of which is not known are measured, the detected values in the channels of the detectors are corrected by the corrected values calculated by the apparatus calibration, and analysis calculation is performed by the corrected detected values.

However, since only the reference values of the respective standard particles of five necessary types are stored, standard particles used for the apparatus calibration may not be easily available. When a standard particle of only one type of the necessary standard particles cannot be obtained, the apparatus calibration for the detectors may not be able to be performed. For this reason, when PSL spheres each having a particle diameter set as the particle diameter of a standard particle are unavailable due to production stoppage, a calibration program for calibrating the detectors must be recomposed to eliminate detection of that missing standard particle diameter.

SUMMARY OF THE INVENTION

The present invention has been made in consideration of the above circumstances, and it is an object to provide a particle diameter distribution measurement apparatus and method which can use standard particles of selected various particle diameters to perform apparatus calibration across a range of particle diameters.

In order to achieve the above object, according to a first aspect of the present invention, there is provided a particle diameter distribution measurement apparatus which includes a plurality of detectors for detecting diffracted lights or scattered lights generated by irradiating a source light to samples to be measured at every angle and which calculates a particle diameter distribution of the samples on the basis of outputs from the detectors, wherein values to be obtained as outputs from the detectors with respect to a plurality of standard particles each having a predetermined particle diameter are stored in a storage unit as reference values, and an apparatus calibration is performed by a standard particle selected from the standard particles from which the reference values are stored.

Therefore, the particle diameters of the standard particles used in calibration of detected values in the detectors can be selected to some extent, and not only a standard particle having one particle diameter but also an available substitute standard particle which can be selected from a plurality of standard particles can be used in apparatus calibration.

According to a second aspect of the present invention, there is provided a particle diameter distribution measurement apparatus which includes: a plurality of detectors for detecting diffracted lights or scattered lights generated by irradiating light to samples to be measured for every angle; a storage unit for storing reference values obtained as outputs from the detectors with respect to standard particles each having a predetermined particle diameter as reference values; and a calculation process unit which can execute a calibration program for measuring the stored standard particles, comparing detected values from the detectors with the reference values to calculate calibration constants for the respective detectors, and storing the calibration constants and a calculation program for measuring an arbitrary sample to be measured and performing analysis calculation on the detected values from the detectors which are corrected by a calibration constant to calculate a particle diameter distribution of the sample to be measured, wherein the storage unit stores the reference values of the plurality of standard particles for one detector, and the calibration program calculates a calibration constant by using the reference value of a standard particle selected from the standard particles the reference values of which are stored and stores the calibration constant.

Therefore, as a standard particle used in calibration, not only a standard particle having one particle diameter but also an available substitute standard particle which is selected from a plurality of standard particles can be used for one detector. Even when certain standard particles are not available, the calibration program need not be recomposed, and the particle diameter distribution measurement apparatus can still cope with the standard particles by changing the data of reference values.

When the reference values of the first aspect of the present invention are stored in the storage unit in units of files corresponding to the standard particles, it is possible to select the standard particles used in the calibration and the standard values of the standard particles on a screen. When the storage unit, according to a second aspect, stores the reference values in units of files corresponding to the standard particles to enable the calibration program to make it possible to select standard particles used in the calibration and the reference values of the standard particles on a screen, the reference values can be easily managed. A user of the particle diameter distribution measurement apparatus easily selects an appropriate standard particle for the calibration, and the appropriate apparatus calibration can be performed.

When the range of the detectors to be calibrated can be set depending on the available standard particles, according to the first aspect, and when the calibration program according to the second aspect can set the range of the detectors to be calibrated depending on the available standard particles, the apparatus calibration can be more accurately performed. The detectors across a wide range can be simultaneously calibrated depending on the type of a standard particle available, and time required for the apparatus calibration can also be shortened.

When the reference values can be added to the storage unit through an external storage medium or data communication means, the particle diameter distribution measurement apparatus can cope with standard particles of various types which will be available in the future by appropriately adding reference values.

BRIEF DESCRIPTION OF THE DRAWINGS

FIG. 2 is a diagram for explaining a screen on which standard particles are changed by using the particle diameter distribution measurement apparatus;

DETAILED DESCRIPTION OF PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a method and apparatus that can be calibrated even if standard particle sizes are missing.

Figure 1:
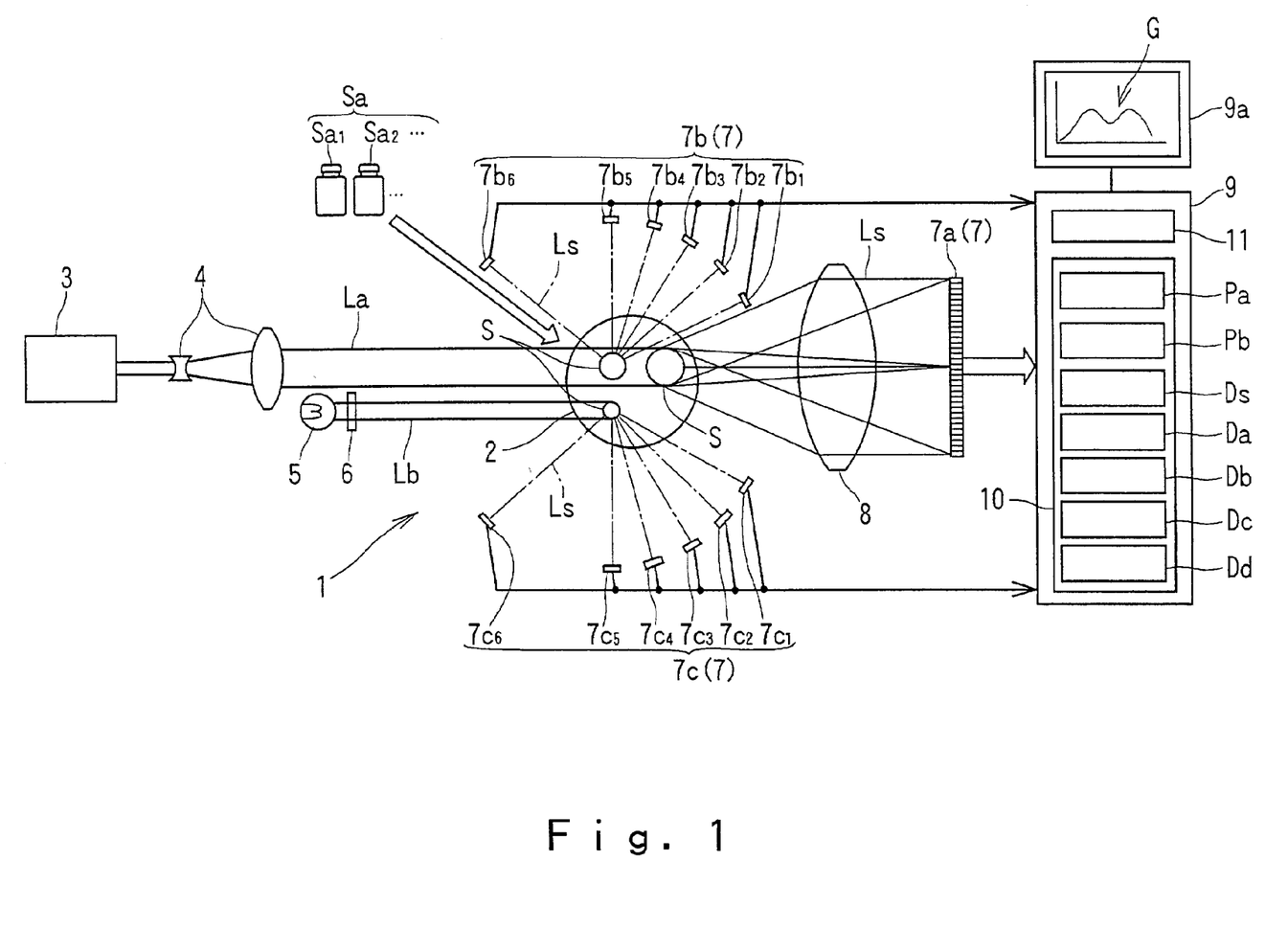
FIG. 1 is a diagram showing the entire configuration of a particle diameter distribution measurement apparatus according to the present invention.

FIG. 1 is a schematic diagram showing a configuration of a particle diameter distribution measurement apparatus 1 according to the present invention. In FIG. 1, reference numeral 2 denotes a cell in which a scattered sample to be measured S is enclosed; reference numeral 3 denotes a light source constituted by an He—Ne laser tube which irradiates a laser beam La onto the cell 2; reference numeral 4 denotes a beam magnifier which magnifies the diameter of the laser beam La; reference numeral 5 denotes a light source constituted by a tungsten lamp which irradiates a parallel light Lb onto the cell 2; reference numeral 6 denotes a filter which remove light having unnecessary wavelengths from the parallel light Lb; reference numeral 7 denotes a detector which detects scattered lights or diffracted lights (scattered or diffracted lights are to be referred to as scattered lights Ls hereinafter) generated by the sample to be measured S; and reference numeral 8 denotes a lens which converges, of the scattered lights Ls, scattered lights Ls generated in a propagation direction of the laser beam La to the corresponding detector 7.

Reference numeral 9 denotes a calculation process device which calculate a particle diameter distribution of the sample to be measured S by using the intensity of the scattered lights Ls detected by the detectors 7. This calculation process device 9 has a storage unit 10 and a process unit 11 which analyzes the intensity of the scattered lights Ls detected by the detectors 7 by using the programs and data stored in the storage unit 10 to calculate the particle diameter distribution of the sample to be measured S. Reference numeral 9a denotes a display unit which displays the calculated particle diameter distribution.

The apparatus configuration of this embodiment is to show an example for the following description and should not limit the present invention. More specifically, the shape of the cell 2 is not limited to a columnar shape and may have a box shape. Similarly, the light sources are not limited to the two types of light sources 3 and 5. The arrangement and the number of detectors 7 and the positions and the types of lenses 14 and 8 are arbitrarily set.

The storage unit 10 can be constituted by an external storage device such as a hard disk drive, a floppy disk drive, a CD-ROM, DVD-ROM and a storage medium such as a semiconductor memory. The storage unit 10 stores reference values (base data) Ds of scattered lights Ls to be detected by the detectors 7 when standard particles Sa (in this embodiment, for example, standard particles $Sa_1$ to $Sa_5$ of five types) each having a predetermined particle diameter are measured as the sample to be measured S, a calibration program Pa which calibrates the particle diameter distribution measurement apparatus 1 by using the base data Ds, and a calculation program Pb which calculates a particle diameter distribution of the sample to be measured S from the detected values of the scattered lights Ls obtained when an arbitrary sample to be measured S is measured.

The storage unit 10 has library data Da in which reference values corresponding to standard particles of at least five types are stored as reference value files such that the particle diameter distribution measurement apparatus can cope with standard particles the number of which is larger than the necessary number (5 in this embodiment) of standard particles used to calibrate the detected values from all the detectors 7.

If the number of reference value files stored as the library data Da increases, the range of the diameters of the standard particles Sa which can be used in apparatus calibration of the particle diameter distribution measurement apparatus 1 can be widened. The particle diameter distribution measurement apparatus can flexibly cope with various circumferences. However, when the reference values of the standard particles Sa of two or more types are prepared for one detector 7 in the library data Da, available standard particles Sa can be selected and used. More specifically, when the range of the detectors 7 which can be calibrated have a plurality of standard particles having an overlapping portion, other standard particles can be selected and used when one standard particle is unavailable due to production stoppage. Thus, if a standard particle is not available and an overlapping range of values for each of the detector channels are stored in the measurement apparatus, then a calibration procedure can still be performed if we have sample particles with diameters that provide overlapping ranges to validate the values in the overlapping range for the adjacent detector of the missing standard particle, even if a peak position value can not be measured.

The reference value files stored in the library data Da are written from an outside source onto the storage unit through an external storage medium such as a floppy disk drive, a CD-ROM, or a DVD-ROM or a data communication means and can be additionally stored. More specifically, the library data Da can be increased in accordance with the availability of the standard particles Sa which are newly produced. The reference values related to unnecessary standard particles Sa can also be deleted.

The base data Ds is formed by the calibration program Pa as reference values to be used in calibration of the apparatus, such that standard particles Sa of five types which can calibrate detected values obtained by all the detectors 7 are selected from the respective standard particles Sa which are registered by a user as a library data Da. More specifically, the base data Ds recorded on the storage unit 10 has data of reference values the number of which is equal to the number obtained by multiplying at least the number (5 in this embodiment) of the standard particles Sa used in the apparatus calibration by the number (90 in this embodiment) of channels of the detectors 7.

Reference symbol Db denotes calibration constant data of the detectors 7 formed by the calibration program Pa. The calibration constant data Db includes constants which are obtained such that detected values actually measured by using the particle diameter distribution measurement apparatus 1 using the respective standard particles Sa as the sample to be measured S are compared with the reference values recorded as the base data Ds to calculate ratios of the detected values and the reference values. In this embodiment, since the number of channels of the detectors 7 is 90, as the calibration constant data Db, 90 constants corresponding to the detectors 7 are obtained. In this embodiment, the calibration constant data is recorded on the storage unit 10 as the calibration constant files Db.

Reference symbol Dc denotes detected value data of the respective detectors 7 obtained by measuring the sample to be measured S by using the particle diameter distribution measurement apparatus 1. The detected value data Dc is stored in the storage unit 10 as measurement files. Reference symbol Dd denotes particle diameter distribution data which is calculated such that the calculation program Pb corrects and analyzes the detected value data Dc by the calibration constant data Db. Therefore, a particle diameter distribution based on the particle diameter distribution data Dd is displayed on the display unit 9a by a graph G and the like.

The detectors 7 are constituted by a plurality of detectors 7a, 7b, and 7c which are fitted in accordance with the angle of the scattered lights Ls. For example, channels Ch01 to Ch77 are assigned to the plurality of detectors 7a arranged in the form of a ring, for detecting forward scattered light Ls generated by the laser beam La, channels Ch78 to Ch83 are assigned to the detectors $7b_1$ to $7b_6$ of the detectors 7b for detecting lateral or backward scattered light Ls generated by the laser beam La, and channels Ch84 to Ch90 are assigned to the detectors $7c_1$ to $7c_6$ of the detectors 7c for detecting lateral or backward scattered lights Ls generated by the parallel light Lb.

The arrangement and the number of the detectors 7 can be appropriately selected, and the number of channels assigned to the detectors 7 can be appropriately selected as a matter of course. However, the number of channels assigned to the detectors 7 are assigned in the order of the detectors 7 arranged from the front to the rear or in the order of the detectors 7 arranged from the rear to the front, so that a signal process (to be described later) can be easily performed.

FIG. 2 is a screen diagram showing an example of the contents of the base data Ds and an example of a set screen W. This set screen W displays a list of reference values Ds (reference values corresponding to the respective standard particles $Sa_1$ to $Sa_5$ are set as $Ds_1$ to $Ds_5$ hereinafter) based on theoretical values obtained by calculating values (detected values) to be output by the respective channels Ch01 to Ch90 of the respective detectors 7a, 7b, and 7c when five standard particles $Sa_1$ to $Sa_5$ (expressed by "Sample 1" to "Sample 5" in Figure) having predetermined particle diameters are measured as the sample to be measured S.

FIG. 2 shows an example in which the respective values $Ds_{101}$ to $Ds_{590}$ of the respective reference values $Ds_1$ to $Ds_5$ are calculated by theoretical calculation according to a Mie scattering theory. However, the reference values $Ds_{101}$ to $Ds_{590}$ are not limited to these theoretical values. More specifically, a standard particle diameter distribution measurement apparatus in which the same optical structure including, for example, the arrangement of the respective detectors 7 of the particle diameter distribution measurement apparatus 1 to be calibrated and the types of the light sources 3 and 5 used in measurement is prepared. When the standard particles $Sa_1$ to $Sa_5$ in the standard particle diameter distribution measurement apparatus are measured, standard detected values calculated depending on outputs (detected values) from the detectors 7 may be used as reference values. In this case, since apparatus calibration for the particle diameter distribution measurement apparatus 1 can be performed in consideration of an influence (influence by scattered lights generated by a phenomenon which is not understood at the present) by the scattered lights Ls which cannot be calculated by theoretical calculation, the calibration can be more accurately performed.

Reference symbols $Ds_{1min}$ to $Ds_{5min}$ denote the minimum values of the channel numbers of the detectors 7 which can be calibrated by the standard particles $Sa_1$ to $Sa_5$, respectively and reference symbols $Ds_{1max}$ to $Ds_{5max}$ denote the maximum values. Therefore, in the example shown in FIG. 2, the detected values obtained by the detectors 7 of the channels Ch81 to Ch90 can be calibrated by the standard particle $Sa_1$. The detected values obtained by the detectors 7 of the channels Ch78 to Ch81 can be calibrated by using the standard particle $Sa_2$.

Similarly, the standard particle $Sa_3$ corresponds to the channels Ch30 to Ch57, the standard particle $Sa_4$ corresponds to the channels Ch8 to Ch30, and the standard particle $Sa_5$ corresponds to the channels Ch1 to Ch8, so that the detected values obtained by the detectors 7 of these channels are calibrated. The ranges of the channels of the detectors 2 calibrated by the respective standard particles $Sa_1$ to $Sa_5$ are appropriately determined depending on a position where the detected scattered lights La are strong (where a reference value is large).

In this embodiment, since the channels of the detectors 7 are sequentially assigned from the front in the irradiation direction of the lights La and Lb, the ranges of the channels of the detectors 7 the detected values of which can be calibrated by the respective standard particles $Sa_1$ to $Sa_5$ (the ranges determined by minimum values $Ds_{1min}$ to $Ds_{5min}$ and maximum values $Ds_{1max}$ to $Ds_{5max}$) can be continuously set, and a calibration process can be easily performed. However, the ranges of the channels of the detectors 7 which can be calibrated may be discontinuously set. For example, it may be selectively set whether the respective channels of the detectors 7 are to be calibrated or not. In this case, various methods such as a method in which check columns for checking the channels to be calibrated are formed on the sides of the cells for displaying the respective reference values $Ds_{101}$ to $Ds_{590}$ may be employed.

Reference symbols $W_1$ to $W_5$ denote windows which show the names of file selected as the respective standard particles $Sa_1$ to $Sa_5$ from the reference value library Da. In this embodiment, as the standard particles $Sa_1$ to $Sa_5$, the reference values of standard particles having particle diameters of 83 nm, 1 μm, 10 μm, 100 μm, and 1000 μm are selected from the library Da. Therefore, for example, reference values $Ds_{101}$ to $Ds_{190}$, the minimum channel $DS_{1min}$, and the maximum channel $DS_{1max}$ are contents expressed by the files of reference value data having a file name "83nm.q01" and registered in the library Da.

Reference symbol Wp denote a pull down selection menu. As shown in FIG. 2, when an operator opens the pull down menu Wp, and if the operator selects the file of reference value data called "83mn.q01", the reference values $Ds_{101}$ to $Ds_{190}$, the minimum channel $DS_{1min}$, and the maximum channel $Ds_{1max}$ are changed in accordance with standard particles each having a particle diameter of 83 nm. More specifically, the calibration program Pa displays a reference value file constituting the library Da on the screen, so that the operator can select standard particles used in calibration on the screen. Therefore, operability is improved, and the operator can easily select the standard particles Sa.

Reference symbol Ba denote a button for storing a setting, and reference symbol Bb denote a button for canceling the setting. The reference values $Ds_{101}$ to $Ds_{590}$, the numeral values $Ds_{1min}$ to $Ds_{5min}$ and the numeral values $Ds_{1max}$ to $Ds_{5max}$ displayed on the respective cells in this set screen W can be freely changed. In the example shown in FIG. 2, a cursor C is displayed on a cell for displaying the reference value $Ds_{511}$. The cursor C can be moved to make it possible to edit the reference values $Ds_{101}$ to $Ds_{590}$ in the respective cells.

The above-described reference values $Ds_{101}$ to $Ds_{590}$ are edited to appropriately change the reference values $Ds_{101}$ to $Ds_{590}$ when an accurate measurement result cannot be obtained by the reference values calculated by a theoretical calculation based on the Mie scattering theory or the reference values calculated by a standard particle diameter distribution measurement apparatus. The editing is performed to appropriately adjust the ranges of the, minimum-values $DS_{1min}$ to $Ds_{5min}$ and the maximum values $Ds_{1max}$ to $Ds_{5max}$. When the reference values $Ds_{101}$ to $Ds_{590}$ displayed on the respective cells are changed, and when the OK button Ba is depressed upon completion of the setting, a pop up window W is opened as shown in FIG. 3.

Figure 3:
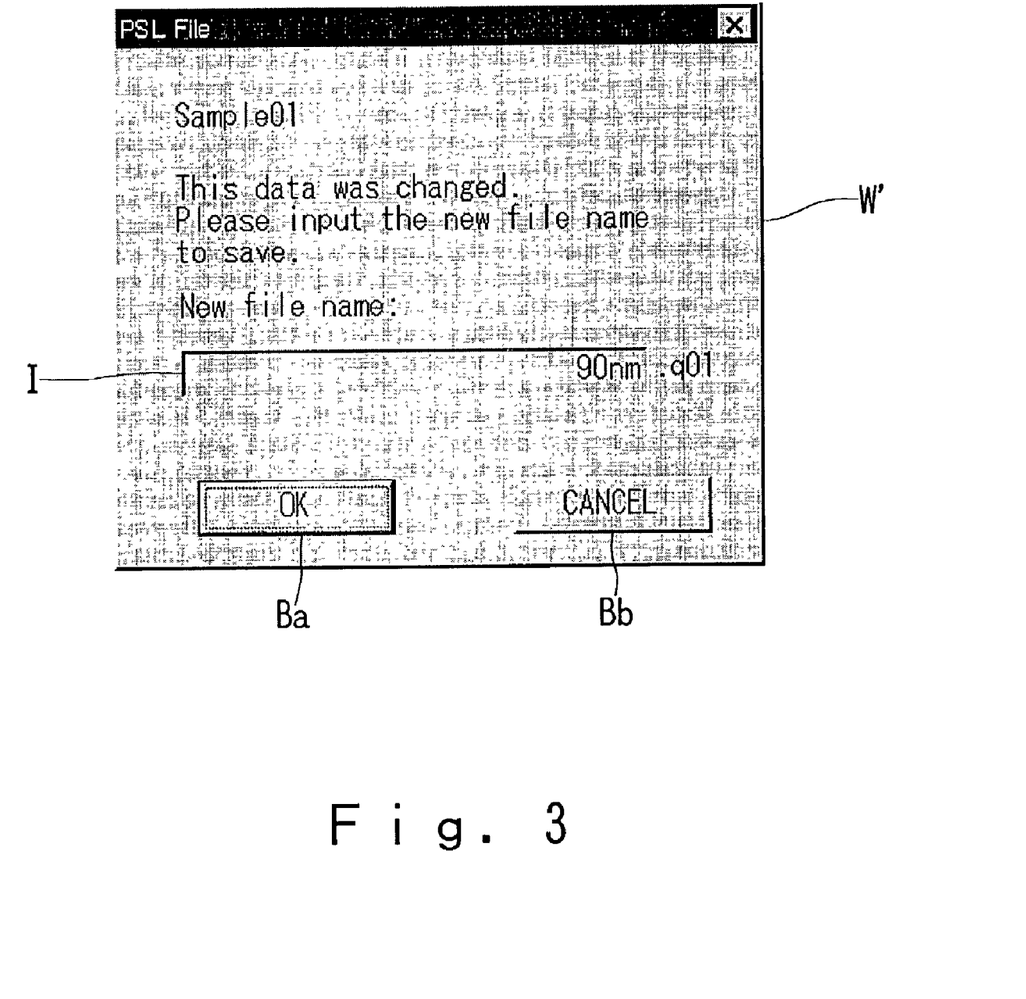
FIG. 3 is a diagram showing another screen on which the standard particles are changed.

FIG. 3 is a diagram showing an example of the pop-up window W displayed when any one of the reference values $Ds_{101}$ to $Ds_{190}$ is changed. In FIG. 3, reference symbol I denotes an input unit in which a new file name is input. In this case, when a new name, for example, "90 nm" is input, a file called "90nm.q01" and having a new reference value is formed and stored in the library Da. More specifically, when the set screen W shown in FIG. 2 is displayed, and when the pull down menu Wp is opened, a newly formed standard particle having a new name of "90 nm" is displayed.

Figure 4:
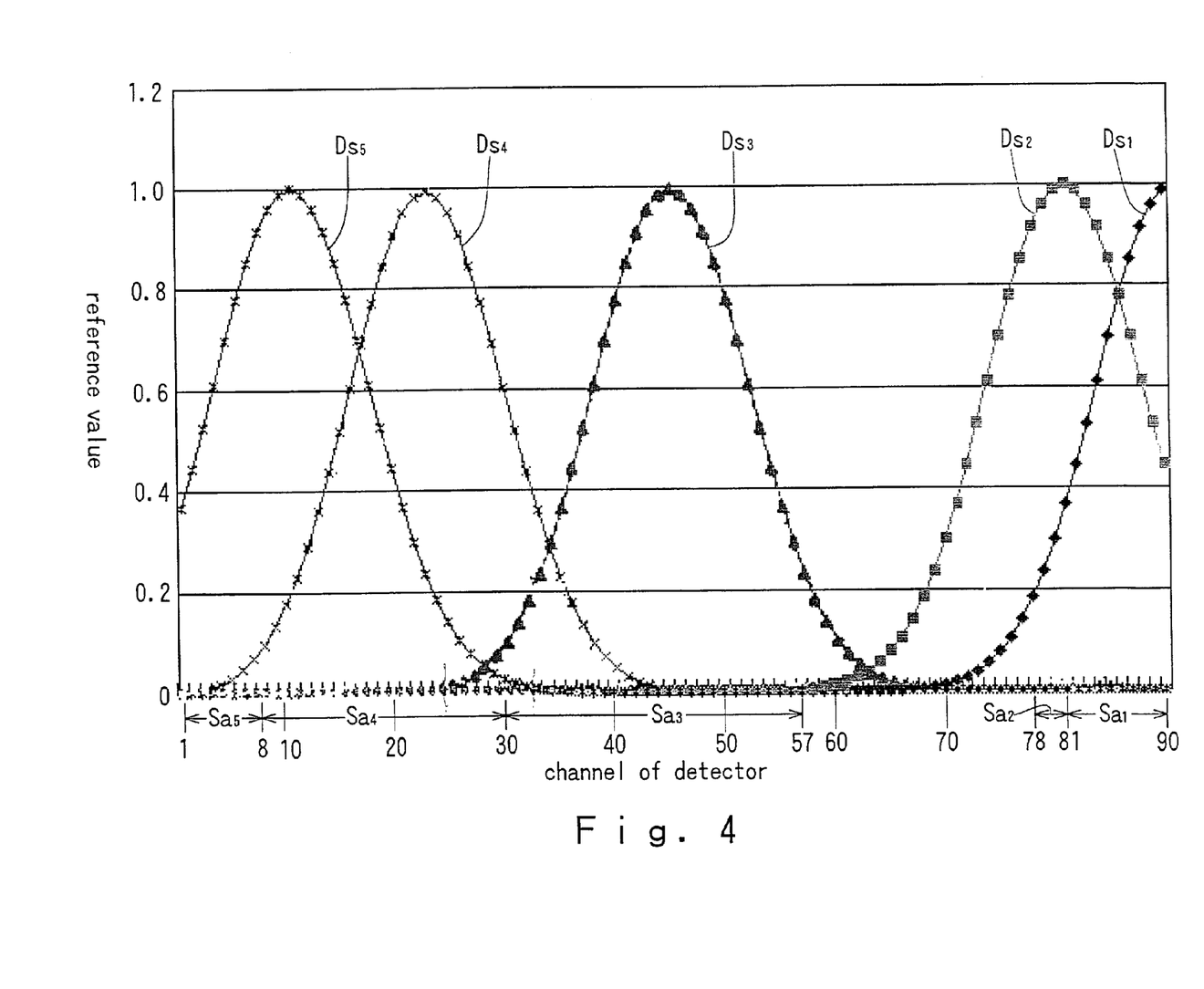
FIG. 4 is a graph showing reference values of detected values obtained when standard particles are used.

FIG. 4 is a graph showing the reference values $Ds_1$ to $Ds_5$ of the respective standard particles $Sa_1$ to $Sa_5$ in this embodiment. The abscissa axis in FIG. 4 shows the channels given to the detectors 7, and the ordinate axis shows the sizes of the reference values corresponding to the detectors 7 of the respective channels.

In the lower column of the abscissa axis, the standard particles $Sa_1$ to $Sa_5$ are shown for calibrating outputs (detected value Dc) from the detectors 7 of the respective channels. As described in FIG. 2, this means that the channels of the detectors 7 which can be calibrated by the standard particles $Sa_1$ to $Sa_5$ are 81 to 90, 78 to 81, 30 to 57, 8 to 30, and 1 to 8, respectively to calculate the ratios of detected values in the channels of several to several tens adjacent of detectors 7. In this case, it is understood that the ranges of the channels of the detectors 7 which can be calibrated by the respective standard particles $Sa_1$ to $Sa_5$ overlap (in this embodiment, the channels 8, 30 and 81 overlap), so that the ratio of an optical intensity distribution of all the detectors 7 can be calculated.

As shown in FIG. 4, the reference value $Ds_1$ obtained when the standard particle $Sa_1$ having a particle diameter of 83 nm is used as the sample to be measured S is used to cause the detectors 7 of the second-half channels subsequent to the channels Ch70 to detect the scattered lights Ls. Similarly, it is understood that the detectors 7 of about 15 channels before and after the channel Ch79 detect the scattered light Ls when the standard particle $Sa_2$ having a particle diameter of 1 μm is measured, it is understood that the detectors 7 of about 15 channels before and after the channel Ch45 detect the scattered light Ls when the standard particle $Sa_3$ having a particle diameter of 10 μm is measured, it is understood that the detectors 7 of about 15 channels before and after the channel Ch25 detect the scattered light Ls when the standard particle $Sa_4$ having a particle diameter of 100 μm is measured, and it is understood that the detectors 7 before the channel Ch25 detect the scattered light Ls when the standard particle $Sa_5$ having a particle diameter of 1 mm is measured.

Therefore, in general, the channels 81 to 90 and 78 to 81, . . . , of the detectors 7 corresponding to the large reference values $Ds_1, Ds_2, \ldots$, of the standard particles $Sa_1$, $Sa_2, \ldots$, are calibrated by using the standard particles $Sa_1$, $Sa_2, \ldots$, so that apparatus calibration can be more accurately performed. In consideration of this point, when the distribution of the reference values $Ds_1, Ds_2, \ldots$, in FIG. 4 is observed, it is understood that the channels of the detectors 7 which can be calibrated by one standard particle $Sa_5$ are not only the channels Ch1 to Ch8, but also the channels Ch1 to Ch20 or more.

A setting of channels calibrated by the respective standard particles $Sa_1$ to $Sa_5$ can be performed by using the set screen W described in FIG. 2, and the calibration program Pa is designed such that the calibration program Pa automatically decides the channels on the basis of the reference values. For example, if the group of detectors lying within the range of channels 9–28, as shown in FIG. 4, can be calibrated by using the standard value $Ds_5$ of standard particle $Sa_5$ and the group of detectors within the range of channels 28–57 can be calibrated by using the standard value $Ds_3$ of standard particles $Sa_3$ so that it becomes possible to provide a calibration of the detectors for the respective channels 1–57, even when the standard particles $Sa_4$ are not available. In this case, however, due to small reference values $Ds_3$ and $Ds_5$ available over the channels 25–32, the accuracy of those channels will be degraded as compared to the remaining channels. More specifically, the calibration program Pa may have such a selection function that the standard particles $Sa_1$ to $Sa_5$ which are most suitable for calibration of the detectors 7 of the respective channels are automatically selected on the basis of the sizes of the reference values $Ds_{101}$ to $Ds_{590}$.

More specifically, in FIG. 4, the data is presented in an easy-to-understand manner for illustration purposes, and the distribution of the reference values $Ds_1, Ds_2, \ldots$ is shown in a moderate distribution having one peak value. However, the distribution of the actual reference values $Ds_1$ to $Ds_5$ is a distribution having a large number of peak values. For this reason, the calibration program Pa automatically selects the standard particles $Sa_1$ to $Sa_5$ which are most suitable for the respective channels of the detectors 7 to make it possible to more accurately perform apparatus calibration. Furthermore, in this manner, the most effective apparatus calibration for the particle diameter distribution measurement apparatus 1 when only a combination of available standard particles $Sa_1$ to $Sa_5$, not available, can be performed.

In any case, since the ranges of the channels of the detectors 7 to be calibrated can be set by the respective standard particles $Sa_1$ to $Sa_5$, the particle diameter distribution measurement apparatus can also cope with any standard particles Sa which may be added in the future.

The detected values obtained by the detectors 7 positioned on the outside of the detectors 7a arranged in the form of a ring like the channels Ch58 to Ch77 is rarely changed by a small difference between light-receiving areas because the areas of the detectors 7 are large. Therefore, in this embodiment, the detected values of the channels Ch58 to Ch77 are not calibrated to make apparatus calibration simple. However, the detected values obtained from the detectors 7 corresponding to the channels Ch58 to Ch77 may also be calibrated.

Figure 5:
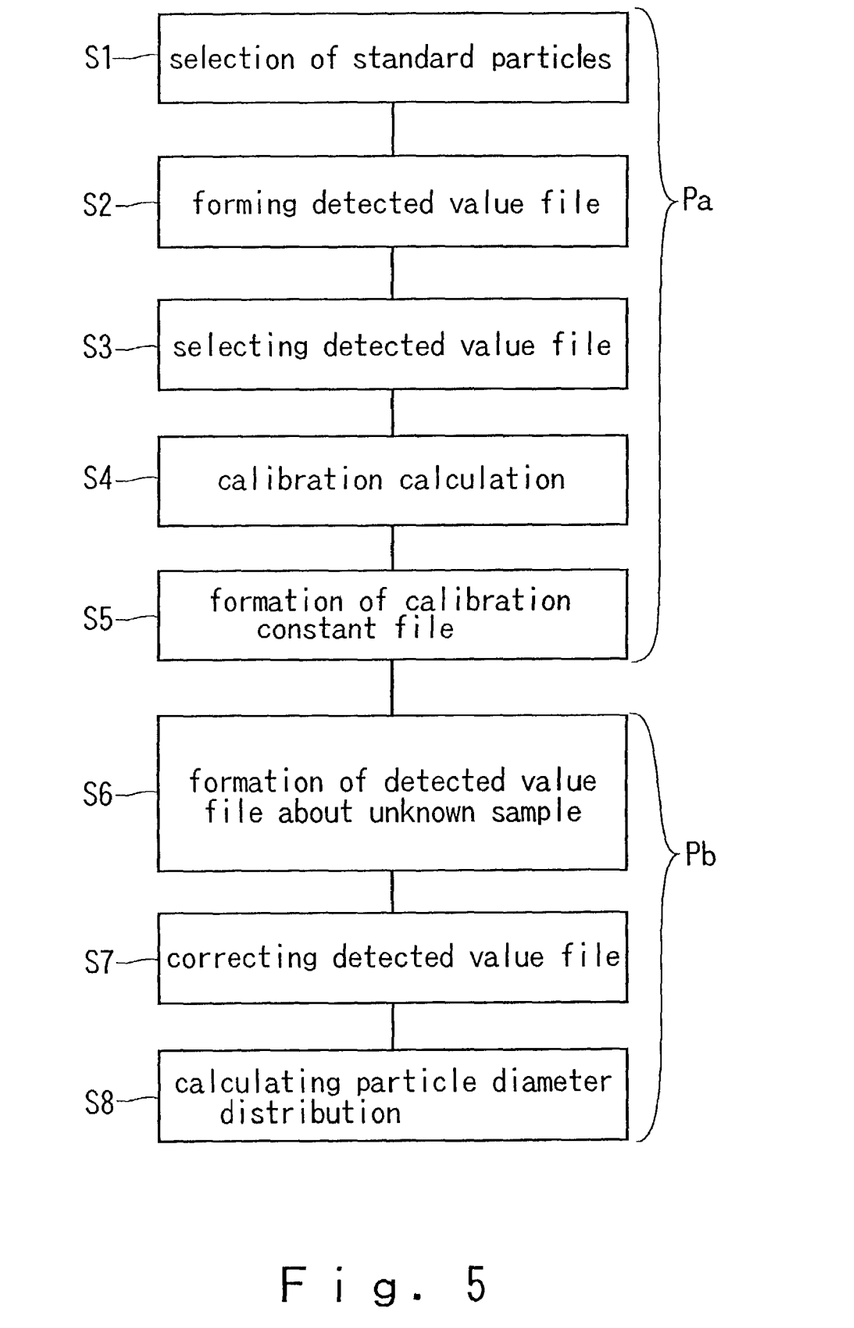
FIG. 5 is a flow chart for explaining an apparatus calibration procedure and a particle diameter distribution measurement procedure using the particle diameter distribution measurement apparatus.

FIG. 5 is a flow chart showing a series of steps from calibration for the particle diameter distribution measurement apparatus 1 to measurement of a particle diameter distribution of the sample to be measured S. More specifically, the apparatus calibration achieved by the calibration program Pa is performed by the procedure shown in steps S1 to S5, and measurement of arm unknown sample achieved by the calculation program Pb is performed by the procedure shown in steps S6 to S8.

Step S1 selects the standard particles $Sa_1$ to $Sa_5$ used in the apparatus calibration. The selection method in step S1 has been described by using FIG. 2. At this time, the particle diameters of the standard particles $Sa_1$ to $Sa_5$ are selected from a plurality of prepared particle diameters, available standard particles $Sa_1$ to $Sa_5$ can be easily selected. In step S1, the ranges of the channels of the detectors calibrated by the respective standard particles $Sa_1$ to $Sa_5$ can also be selected. The plurality of standard particles Sa in which the reference values Da are stored are arbitrarily combined, so that the apparatus calibration can be performed.

Step S2 is a step of forming a detected value file Dc by actually using the respective standard particles $Sa_1$ to $Sa_5$. In this case, in this embodiment, when the standard particles $Sa_1$ to $Sa_5$ of five types are measured as the sample to be measured S, the detected value file Dc consisting of detected values detected by the channels of the respective detectors 7 is formed and recorded in the storage unit 10.

Step S3 is the step of selecting the detected value file Dc used in calibration. Step S4 is the step of performing a calibration calculation which compares the reference values $Ds_{101}$ to $Ds_{590}$ of the standard samples $Sa_1$ to $Sa_5$ selected in step S1 with the detected value file Dc selected in step S3 to calculate ratios of the reference values to the detected value file Dc. The ratios calculated here serve as calibration constants. The calibration performed in step S4 includes calibration of the sensitivities of the respective detectors 7 and calibration of a matching of the particle diameter distribution measurement apparatus 1 including a difference between the quantities of the lights La and Lb obtained from the light sources 3 and 5.

Step S5 is the step of recording all the calibration constants which are the ratios calculated by the calibration calculation in step S4 on the storage unit 10 as a calibration constant file Db at once. The formation of the calibration constant file Db ends the calibration process. More specifically, only the processes in steps subsequent to step S6 may be performed in measurement of a normal particle diameter distribution.

The calibration process using the calibration program Pa is performed for the particle diameter distribution measurement apparatuses 1 one by one in manufacturing the particle diameter distribution measurement apparatuses 1 or before the particle diameter distribution measurement apparatuses 1 are shipped. However, after the particle diameter distribution measurement apparatuses 1 are shipped, the calibration process need not be periodically performed on the particle diameter distribution measurement apparatuses 1 unless the components such as the light sources 3 and 5 and the detectors 7 constituting the optical systems are exchanged or adjusted. However, when the calibration process is periodically performed at predetermined intervals, influences by aging of the components can be corrected, and a particle diameter distribution can be more accurately measured.

Step S6 is the step of measuring the sample to be measured S, the particle diameter distribution of which is unknown, to record the detected values of the respective detectors 7 when the sample to be measured S is measured on the storage unit 10 as the detected value file Dc.

Step S7 is the step of correcting the detected values recorded as the detected value file Dc calculated in step S6 by using the calibration constant file Db.

Step S8 is the step of calculating a particle diameter distribution by using the corrected detected value file Dc on the basis of the Mie scattering theory or the like. In this manner, the particle diameter distribution of arm unknown sample to be measured S is recorded on the storage unit 10 as the particle diameter distribution data Dd. A graph G of the particle diameter distribution is displayed on the display unit 9a according to the particle diameter distribution data Dd.

More specifically, by using the particle diameter distribution measurement apparatus 1 according to the present invention, the standard particles $Sa_1$ to $Sa_5$ used in apparatus calibration for the particle diameter distribution measurement apparatus 1 can be appropriately selected from the plurality of standard particles Sa registered in the library Da. Therefore, when the standard particles $Sa_1$ to $Sa_5$ which have been used in apparatus calibration are not easily available due to production stoppage or the like, the apparatus calibration can still be performed by using other available standard particles.

If the library Da includes no available standard particles, when the reference value files of available standard particles are added to the library Da, the contents of the calibration program Pa and the calculation program Pb need not be changed at all. Therefore, the particle diameter distribution measurement apparatus can rapidly cope with new standard particles. As a method of adding reference value files to the library Da, an external recording medium such as a floppy disk may be used. However, it is desirable that the reference value files can be downloaded from the manufacturer of the particle diameter distribution measurement apparatuses 1 through the Internet™.

In the above embodiment, the standard particles $Sa_1$ to $Sa_5$ of five types are used as standard particles for calibration of the particle diameter distribution measurement apparatus 1. However, in the present invention, the number of standard particles is not limited to a specific number. More specifically, the number of types of standard particles may be 4 or less or 6 or more depending on the configuration of the particle diameter distribution measurement apparatus 1, a measurement range of a particle diameter distribution, and particle diameters included in the particle diameters of the standard particles.

Similarly, in the above embodiment, for the sake of descriptive convenience, the calibration program Pa and the calculation program Pb which can be executed by the process unit ii are separately expressed. However, the calibration program Pa and the calculation program Pb need not be separated from each other. Although the data Da to Dd and Ds are disclosed for description, the present invention does not limit the existence of the files.

As has been described above, according to the present invention, even though standard particles having particle diameters determined for apparatus calibration for the particle diameter distribution measurement apparatus are not available, the apparatus calibration can be performed by changing the standard particles. The particle diameter distribution measurement apparatus can further easily cope with new standard particles which will be produced in the future by adding reference value data without changing programs or the like, and can perform apparatus calibration.

What is claimed is:

1. A particle diameter distribution measurement apparatus, which includes a plurality of detectors for detecting diffracted lights or scattered lights generated by irradiating light to samples to be measured and which calculates a particle diameter distribution of the samples on the basis of outputs from the detectors, comprising:
    means for storing values to be obtained as detector outputs from the plurality of detectors with respect to a plurality of standard particles, the detector outputs are within predetermined ranges and are stored in a storage unit as reference values; and
    means for providing an apparatus calibration performed by only a standard particle selected from the plurality of standard particles, the reference values of which are stored, wherein the range of detectors to be calibrated is set depending on the standard particles available.

2. The particle diameter distribution measurement apparatus according to claim 1, wherein the above reference values are stored in a storage unit in units of files corresponding to the standard particles to enable a selection of the standard particles used in the calibration and the display of the standard values of the standard particles on a screen.

3. The particle diameter distribution measurement apparatus according to claim 2, wherein the reference values can be added to the storage unit through an external storage medium or data communication means.

4. A particle diameter distribution measurement apparatus, which includes a plurality of detectors for detecting diffracted light or scattered light generated by irradiating light to samples to be measured; a storage unit for storing values obtained as outputs from the detectors with respect to standard particles each having a predetermined particle diameter as reference values; and a calculation process unit which can execute a calibration program for measuring the stored standard particles, comparing detected values from the detectors with the reference values to calculate calibration constants for the respective detectors, and storing the calibration constants and a calculation program for measuring an arbitrary sample to be measured and performing analysis calculation of the detected values from the detectors which are corrected by the calibration constant to calculate a particle diameter distribution of the sample to be measured, comprising:
    reference values for a plurality of standard particles for each detector are stored in the storage unit, wherein the storage unit stores the reference values in units of files corresponding to the standard particles to enable the calibration program to select standard particles used in the calibration and to display the reference values of the standard particles on a display screen; and
    a controller for executing the calibration program to calculate a calibration constant for each detector by using the reference value of two or more standard particles selected from the plurality of standard particles, the reference values of which are stored, and storing a calibration constant for each detector wherein the above calibration program can set the range of the detectors to be calibrated depending on two or more standard particles.

5. The particle diameter distribution measurement apparatus according to claim 4, wherein the reference values can be added to the storage unit through an external storage medium or data communication means.

6. A method of calibrating a particle diameter distribution measurement apparatus with a plurality of standard particles of different sizes, comprising the steps of:
    storing calibration values for a plurality of standard particle sizes representative of detector outputs across a range of detection for a plurality of detectors;

selecting standard particle sizes with overlapping ranges of detection; and calibrating the particle diameter distribution measurement apparatus by measuring at least one standard particle size and verifying the validity of a range of detection which includes within the range of detection a standard particle size not available to calibrate the particle diameter distribution measurement apparatus.

7. A particle diameter distribution measurement apparatus comprising:

a sample cell;

a source of light to irradiate the sample cell;

a plurality of detectors positioned operatively adjacent the sample cell to measure light interacting with a specimen in the sample cell;

a storage unit for storing predetermined values representative of outputs of the detectors for a plurality of predetermined standard particle sizes, the representation outputs for individual standard particle sizes of the plurality of predetermined standard particle sizes, extend across a range of detection for the plurality of detectors; and a controller unit for calibrating the particle diameter distribution measurement apparatus with a number of predetermined standard particles of different sizes less than the plurality of predetermined standard particle sizes by measuring at least one standard particle size in the sample cell and verifying the validity of a range of detection for a standard particle size, from the plurality of predetermined standard particles, that is not available for calibration.

8. In a particle diameter distribution measurement apparatus, which includes a plurality of detectors for detecting diffracted light or scattered light generated by irradiating light to samples to be measured; a storage unit for storing values obtained as outputs from the detectors with respect to standard particles each having a predetermined particle diameter as reference values; and a controller which can execute a calibration program for measuring the stored standard particles, comparing detected values from the detectors with the reference values to calculate calibration constants for the respective detectors, and storing the calibration constants and a calculation program for measuring an arbitrary sample to be measured and performing analysis calculation of the detected values from the detectors which are corrected by the calibration constant to calculate a particle diameter distribution of the sample to be measured, the improvement comprising:

a greater number of reference values than necessary for calibration of the plurality of detectors including reference values for at least two or more types of standard particles per detector are stored in the storage unit, whereby the controller executes the calibration program to thereby find and store calibration constants for the plurality of detection by selectively using those stored reference values which can calibrate all of the detection values of the plurality of detectors from the available multiple standard particles, entered in the controller, whose reference values are stored in the storage unit.

9. A calibration system for a particle diameter distribution measurement apparatus including a sample cell, a source of light to irradiate the sample cell, and a plurality of detectors positioned operatively adjacent the sample cell to measure light interacting with a specimen in the sample cell, a majority of the plurality of detectors are capable of outputting signals representative of at least two different sizes of particles, comprising:

a storage unit for storing calibration values representative of outputs of the detectors for a plurality of standard particles of different sizes, the representation outputs extend across a range of detection of the different particle sizes for the plurality of detectors;

a set of standard particles of different sizes that are less than an optimum number of standard particles for calibrating the entire range of detection for the plurality of detectors; and a controller unit for calibrating the particle diameter distribution measurement apparatus with the set of standard particles of different sizes by measuring at least one standard particle size in the sample cell and verifying the validity of the range of detection for a standard particle size measurement that is not available in the set of standard particles.

* * * * *